(12) United States Patent
Samuels

(10) Patent No.: US 7,295,308 B1
(45) Date of Patent: Nov. 13, 2007

(54) AIR SAMPLING METHOD AND SENSOR SYSTEM FOR SPECTROSCOPIC DETECTION AND IDENTIFICATION OF CHEMICAL AND BIOLOGICAL CONTAMINANTS

(75) Inventor: Alan C. Samuels, Havre de Grace, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 58 days.

(21) Appl. No.: 11/250,703

(22) Filed: Oct. 13, 2005

Related U.S. Application Data

(63) Continuation of application No. 10/359,494, filed on Feb. 6, 2003, now Pat. No. 6,985,818.

(51) Int. Cl.
*G01J 3/28* (2006.01)
(52) U.S. Cl. .................................. 356/326; 356/301
(58) Field of Classification Search ................ 356/301, 356/302, 303, 319, 326
See application file for complete search history.

(56) References Cited

U.S. PATENT DOCUMENTS 5,866,430 A * 2/1999 Grow ........................ 436/172

2004/0021860 A1 * 2/2004 Gardner et al. ............. 356/301

* cited by examiner

*Primary Examiner*—Roy M. Punnoose
(74) *Attorney, Agent, or Firm*—Ulysses John Biffoni

(57) ABSTRACT

A continuous monitoring method and system wherein a porous substrate or film is used. The air from the environment is drawn through a region of the porous substrate by a simple air pump and the substances in the air are deposited or chemically adsorbed onto the surface of the substrate. The region of the substrate where the environmental air is drawn through is continuously monitored by an optical or spectrometric method. The substrate is in the form of a tape supplied by a feed reel in a reel-to-reel cartridge and taken up by a take-up reel as found in a film cartridge or a magnetic tape cartridge. The cartridge can be replaceable. A variety of materials may be employed as the substrate with an adequate surface area to effect accumulation of solid, liquid, aerosol, or gas phase compounds. An optical interrogation system is engineered such that the surface of the tape at the point where air from the environment is drawn through the substrate becomes the interaction region between the source output and the sample. As material from the environment accumulates in this region, the interaction of the source with the material is monitored by a suitable detector and supporting circuitry.

15 Claims, 3 Drawing Sheets

AIR SAMPLING METHOD AND SENSOR SYSTEM FOR SPECTROSCOPIC DETECTION AND IDENTIFICATION OF CHEMICAL AND BIOLOGICAL CONTAMINANTS

This application is a continuation of application Ser. No. 10/359,494 filed Feb. 6, 2003, now U.S. Pat. No. 6,985,818.

GOVERNMENT INTEREST

The invention described herein may be manufactured, used and licensed by or for the U.S. Government.

BACKGROUND OF THE INVENTION

1. Field of the Invention

The present invention relates to an air sampling method and sensor system for spectroscopic detection and identification of chemical and biological contaminants. More specifically, the invention relates to a porous film composed of select materials to be used as an environmental sampling tool for optical and/or spectroscopic interrogation of captured solid (e.g., dust or asbestos particles), liquid (e.g., chemical warfare agents), liquid-aerosol (e.g., oil droplets), and gas phase atmospheric constituents (e.g., volatile organic compounds).

2. Brief Description of Related Art

The process of environmental monitoring for hazardous materials presents numerous technical challenges. To date, no single platform has been shown to be capable of reliably detecting and identifying all known hazardous materials that may be present in the atmosphere. The presence of most materials can be assessed through the sequential application of a variety of analytical techniques, many of which involves the use of costly instruments, expensive reagents with limited shelf lives, and more often than not, a highly trained technician to operate the sensor, and collect and prepare the sample for detailed analysis. In the present art, a variety of environmental samples may be collected into a solution phase for further preparation or onto a solid phase adsorbent for subsequent thermal desorption and analysis. The former method (solution phase collection) is useful for particulate samples whereas the latter method (solid phase adsorption followed by collection) is applicable only to gas phase substances such as volatile organic compounds. In either case, the sample is modified somewhat by these procedures, and detection is done in a batch rather than real time mode of operation.

Mass spectrometry has been applied in a role that is somewhat related to the present collection method; however, in mass spectrometry, the sample is collected on a movable tape by impaction, which only captures solid and "sticky" liquid aerosols, and the sample must be moved into the mass spectrometer ionization chamber for interrogation at fixed time intervals rather than by a continuous real-time sampling system. Impaction is a mechanical means of capturing particulates from an air stream, by impacting the particles onto a flat surface using a high velocity airflow. It is used in air monitoring applications.

The following U.S. Patents relate to environmental air sampling and/or detection and identification of contaminants:

U.S. Pat. No. 6,405,137 (June 2002) describes a thermal imaging microscopy analysis tool only. Sample preparation is not discussed and samples must be desorbed from their substrate to be analyzed chemically by some standard chemical analysis instrumentation.

U.S. Pat. No. 6,393,085 (May 2002) describes a neutron scattering system. Sample preparation is not described, but system analyzes bulk samples.

U.S. Pat. No. 6,379,623 (April 2002) describes a piezoelectric system that emits light determined by oscillation frequency of the piezo. The system requires a separate, highly specific activation layer coating the crystal, and assumes that detection would be effected by noting the specific patterns of adsorption onto the layer, as for example is done with surface acoustic wave sensors.

U.S. Pat. No. 6,327,184 (April 2002) describes a detector based on paper impregnated with dyes that change color in the presence of liquid chemical agents. The color change is photometrically monitored in an automated fashion.

U.S. Pat. No. 6,351,983 (March 2002) describes a portable gas chromatograph and mass spectrometer used to detect and identify chemicals in the gas phase.

U.S. Pat. No. 6,314,793 (November 2001) describes a device that quantitatively draws ambient air into a chamber for analysis of gas phase materials using a separate chemical detector system appropriate for the chemical to be detected.

U.S. Pat. No. 6,305,213 (October 2001) describes a gas phase detection and identification system that relies on spectrophotometry to identify chemical vapor species by virtue of their spectral fingerprints. The chemical is separated by gas chromatography prior to being delivered to this sensor.

U.S. Pat. No. 6,277,651 (August 2001) describes a wafer-based detector comprising a diode laser in the wafer and antibodies or DNA fragments that bind specific analytes to the wafer surface. The binding event is recognized by a detector that monitors the diode laser illumination.

U.S. Pat. No. 6,237,397 (May 2001) describes an acoustic wave sensor that monitors an adsorbent for a change in mass caused by absorbents. The surface must selectively adsorb materials in order to effect unambiguous identification.

U.S. Pat. No. 6,212,939 (April 2001) describes uncoated cantilevers illuminated by a scanned-wavelength photon source. The photon source excites change carriers into or out of the surface states depending on the electronic energy levels of any adsorbed materials.

U.S. Pat. No. 6,100,975 (August 2000) describes a Raman spectrometer using an external cavity laser source and a sample cell that is monitored by the spectrometer. The cell is a flow-through design and does not collect, pre-concentrate, or archive samples.

U.S. Pat. No. 6,087,183 (July 2000) describes an air sampling system consisting of a thin fluid film across which air is circulated. In the process, particulates and soluble organic substances may be analyzed by some suitable analytical method to detect and identify the contaminants. The patent suggests photometric or electro-analytical methods for such analyses.

In summary, there is a need for a sampling method and sensor system for spectroscopic detection and identification of chemical and biological contaminants that reliably detects and identifies all known hazardous materials in the atmosphere in a real time mode of operation without modification of the sample.

It is therefore an object of the present invention to provide a sampling method and sensor system that quickly identifies hazardous materials in the atmosphere in a real time mode of operation.

It is a further object of the present invention to provide a sampling method and sensor system that does not modify the sample.

It is still a further object of the invention to provide a sampling method and sensor system that can collect and identify liquid, gaseous and solid materials from the environment in a single step onto a single substrate.

It is still a further object of the invention to provide a sampling method and sensor system that is capable of demarcating the substrate so that various sampling areas on the substrate can be archived and retrieved for further analysis in a forensic laboratory or entered as forensic evidence.

These and other objects of the invention will become apparent upon further reading of this disclosure.

SUMMARY OF THE INVENTION

The present invention relates to a method for physically and physico-chemically accumulating atmospheric constituents such as aerosols, volatile organic compounds, and any chemical or biological substance in solid, liquid, aerosol, or gas form onto the surface of a sampling substrate for optical interrogation.

The substrate is manufactured in the form of a porous membrane such that the atmosphere to be sampled can be drawn through the substrate with the use of an ordinary diaphragm pump or other appropriate air sampler. The interaction region of the optical or spectrometric analytical system is aligned to the sampling area of the substrate so that adsorbed and or trapped materials are interrogated by the analytical method at a sampling area. The background and or baseline response of the analytical system is collected against a pristine area of the substrate. The response of the analytical system is collected and digitized as the atmosphere is drawn through the substrate to monitor the accumulation of solid, liquid aerosol or chemisorbed gases on the substrate surface.

The spectral response of the system is compared to the spectral properties of analytes of interest using a suitable algorithm such as a statistical correlation, multivariate analysis, or spectral matched filter for detection that incorporates a database such as for example, the Edgewood Chemical Biological Agent Simulant Knowledge database of spectral properties of the target analytes relevant to the interrogation method.

The substrate film is advanced to an adjacent pristine area when such conditions occur as saturation of the spectral signal, detection of an analyte of interest, or other conditions as deemed appropriate by the user. For each individual use of the monitoring device and method, the speed of the tape is adjusted depending on the surrounding conditions. If the air is particularly dusty or full of contaminants, the tape would be adjusted to move faster than if the air had relatively few contaminants. In any case, the actual spectroscopic sensing method employed by the sensor could serve as a metric for saturation and control the movement of the tape to an unsaturated region.

The substrate is packaged in the form of a reel-to-reel tape in a cartridge format so that it is easy to replace the system in the analytical device. The surface of the substrate is demarcated with an optical, mechanical, or magnetic media so that archived portions of the substrate can be automatically retrieved for further analysis in a forensic laboratory or entered as forensic evidence.

DETAILED DESCRIPTION

Figure 1:
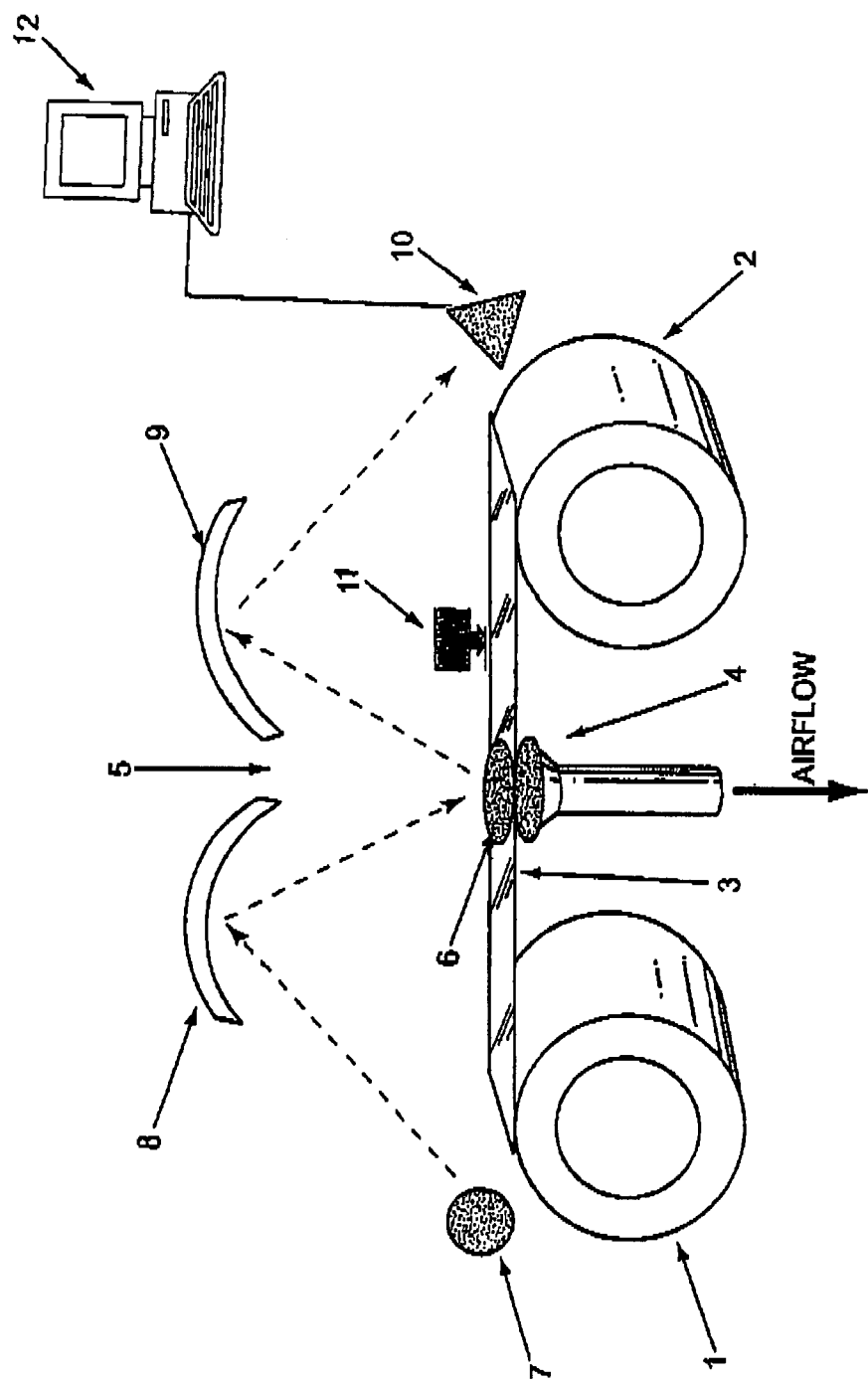
FIG. 1 is an exemplary implementation of the collection method.

The present invention is directed to a continuous monitoring method and system wherein a porous substrate or film is used as a sampling tool. The air from the environment is drawn through a region of the porous substrate and the substances in the air are deposited or chemically adsorbed onto the surface of the substrate. Substances in the air of interest are biological warfare agents, chemical warfare agents, industrial chemicals and materials, various other toxic substances or any substance of interest. The region of the substrate where the environmental air is drawn through is continuously monitored by an optical or spectrometric method.

The invention uses a solid substrate in the form of a tape supplied by a feed reel and taken up by a take-up reel as found in a film cartridge or a magnetic tape cartridge. The tape is formed from a microporous material that is permeable to air to which a variety of materials may be attached with an adequate surface area to effect accumulation of solid, liquid, aerosol, or gas phase compounds. A simple example of such a material that is useful for mid infrared spectra is a silver metal membrane filter that is commonly used in microbiological assays. The surface may be modified physically (e.g., by thermal cycling, polishing, irradiation) or chemically (e.g., by electrochemical or chemical etching, attachment of molecules to the surface, or coating with adsorbent substrates) to increase the surface area and provide other properties, such as specific affinity towards analytes of interest or concern. As another example in the instance where the system uses near infrared spectroscopy, a paper or alumina material is appropriate as a substrate. When X-ray, fluorescence, Raman spectroscopy or other spectrometric methods are used, appropriate substrates that are known to be useful for each particular spectral range may be employed.

An example of a suitable thickness of silver membrane film is 10-50 microns thick. The preferred thickness is 30 microns. The material should also be flexible for use on a reel-to-reel mechanism.

In another embodiment of the invention, the substrate may be bifurcated into materials that are better suited to solid or liquid adsorption or aerosol absorption. In this embodiment, a single substrate in the form of a tape may contain various regions side by side of varying materials, such as a material known for good absorption of solids, a material known for good absorption of liquids and a material known for good adsorption of gases. In other words, the tape may be formed of one or more materials that are known in the art for particular types of absorption. An example of such a bifurcated composition for use in mid infrared spectrometric analysis would be a porous silver membrane that is pure along one half of its length, and impregnated with a metal oxide such as magnesium oxide along the other half of its length. The pure length of the membrane would trap solid particulate materials while the impregnated length of the same membrane would adsorb volatile organic compounds from the vapor or liquid state so that their infrared spectra would appear against the otherwise transparent metal oxide substrate.

The tape is routed over the intake port of a simple air pump as provided by a diaphragm pump or other such suitable device for drawing air from the environment into the device.

A suitable source of electromagnetic radiation is directed to the subject device to provide illumination and in some implementations the source itself may be modulated to enhance the signal level or to effect multiple wavelength spectral resolution as with Fourier transform spectroscopy. An optical interrogation system is engineered such that the surface of the tape at the point where air from the environment is drawn through the substrate becomes the interaction region between the source output and the sample as depicted in FIG. 1. Multiple optical methods may be used concurrently, both engineered to interrogate the same collection region, to provide independent detection schemes that allow the system to self-confirm detection events. For example, an infrared diffuse reflectance measurement can be performed along one axis and a Raman scattering measurement along another (e.g., orthogonal) axis. Other combinations may also be implemented such as Raman/fluorescence, Raman/LIBS, etc. As material from the environment accumulates in this region, the interaction of the source with the material is monitored by a suitable detector and supporting circuitry. In some implementations, the detector may consist of a dispersive element such as a prism or grating or a tunable bandpass filter such as a Fabry-Perot etalon such that resolution of the wavelength dependence of the optical signal resulting from the interaction of the source with the accumulated sample can be effected.

Finally, the output of the detector is digitized through the use of a suitable set of signal preamplifiers and analog-to-digital circuitry. This data may be stored in a microcomputer system for archival purposes or for immediate processing using a detection algorithm. In all cases, a pristine area of the tape is interrogated by the system before the sensor starts collection of materials from the air environment. This interrogation of the clean substrate affords an initial baseline or background signal level for the sensor.

As air containing solid particulates, liquid droplets, aerosols, or gaseous contaminants is drawn through the tape, these materials accumulate by adsorbing chemically onto the surface of the tape or in the case of solid particulates, the solids simply become trapped by the microporous material. The spectroscopic sensor continuously monitors the accumulation of material on the surface of the tape, and the identity of such material can be deduced by comparing the spectral response of the sampled material with that from a spectral library. A database can be created of a library of known atmospheric constituents by drawing known atmospheric constituents through the sampling substrate and interrogating said constituents with an optical or spectrometric interrogation device to obtain a known spectral response thereof. Other databases of spectra are available from Government agencies such as NIST and EPA, and commercially, from companies such as Sadtler, Aldrich, Infrared Analysis, etc. Practitioners in the art of spectroscopy use these databases routinely.

This process may be automated to some extent, particularly in cases where a finite number of target materials to be monitored are programmed into the spectral library of the sensor and a suitable algorithm operates on the signal acquired by the sensor.

Furthermore, a "running" or moving background method may be implemented in the signal processing to reduce or eliminate the effect of indigenous atmospheric constituents that may accumulate on the surface of the tape during routine operation of the sensor in an uncontaminated environment.

The sensor system as described herein may be calibrated in terms of the airflow rate and the spectral signal intensity such that both qualification and quantification of the target analyte may be effected. For example, the system may be designed to draw one liter of air per minute while monitoring the spectral absorption level of a given analyte. As long as a quantitative absorption spectrum of the analyte of interest is contained in the sensor system's electronic database, then the shape of the measured spectrum may be matched to that of the database spectrum for qualitative identification while the intensity of the measured spectrum may be compared (e.g., ratiometrically) to determine the quantity detected as a function of time. The total concentration of the analyte in the monitored air can then be estimated by computing the total number of liters of air drawn through the filter.

In addition, the sensitivity limits of the spectroscopic method impose limitations on their ability to detect and identify analytes, as material accumulates on the surface of the tape it increases in local concentration, facilitating the detection and identification of low levels of the analyte or analytes of interest. Under most spectroscopic methods, the interrogation process is either non-destructive or at least not wholly destructive such that much or all of the analyte that accumulates on the tape remain on the tape after the sensor effects interrogation of the analyte. The tape can be coded mechanically or electronically as with, for example, with a bar code system or magnetic media, to mark the location of the analyte, particularly in those cases where the detection algorithm indicates the presence of an analyte of interest at a threshold concentration level set by analytical laboratory for validation of the identity of the material.

All sample collection systems are subject to fouling either by accumulating dust, oil, or other innocuous substances from the sensor environment during the normal operation of the device. The tape described in this invention has the quality that as the signal levels become saturated when the interrogation region accumulates various materials, or in cases where solids accumulate in the pores and reduce the flow-rate through the porous membrane, then the tape can be advanced to a clean area, and the operation of the sensor can continue after a new baseline measurement is effected.

The detection limit of the spectrometric method can be enhanced by the concentration function (i.e., the accumulation of analytes from a large volume into a small area) of the substrate and collection system.

FIG. 1 is a detail of the concept for an air sampler and sensor for spectrometric detection and identification of chemical and biological contaminants. A substrate feed reel 1, a substrate uptake reel 2, and a porous adsorptive substrate 3 consisting of air permeable micropores and a high surface area material to which chemicals can adsorb are shown. This material will be further chosen such that its spectroscopic properties do not interfere with the fingerprint spectral patterns found in organic chemicals and biological materials (such a choice of materials is a routine procedure for practiced spectroscopists). An air intake 4 leads to a diaphragm pump or other suitable low-pressure environment such that the air is drawn from the environment 5 through an interrogation region 6 on the surface of the substrate 3. A spectrometer light source 7 is shown in this implementation. It may be a modulated thermal source as in Fourier transform infrared spectroscopy, a tunable diode source for infrared spectroscopic measurements, a laser source for Raman, laser-induced breakdown, Brillouin spectroscopy, fluorescence spectroscopy, or other laser-based spectrometric methods, or another light source such as an x-ray source for x-ray fluorescence, any light source operating in the optical through microwave spectroscopic region for dielectric spectroscopy, or other source as appropriate to other types of spectroscopy or spectrometry. Also shown are a focusing optical or pseudo-optical device 8 such as a concave mirror that collects radiation from the source 7 and directs it to a spot on the substrate 3 to fill the interrogation area 6, and another focusing optic 9 that collects radiated energy from the surface of the substrate 3 at the interrogation area 6 and focuses it on the detector 10. Finally, also shown are demarcating device 11 and computer 12 interfaced to said detector 10.

Figure 2:
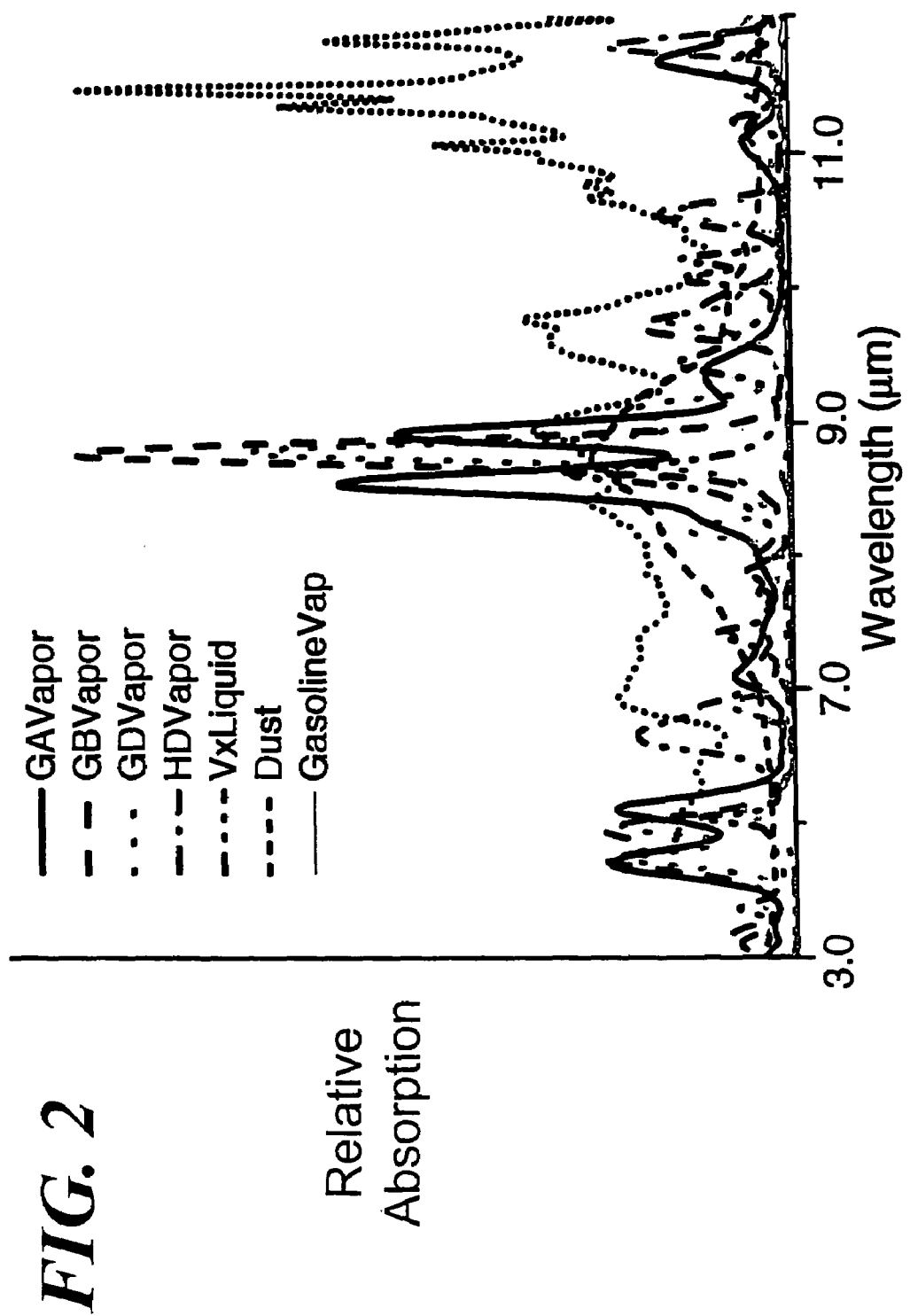
FIG. 2 is a series of infrared spectra of materials of interest for detection and identification in military contamination avoidance applications as well as some interferants including gasoline and dust.

FIG. 2 shows infrared spectra of some chemical materials of interest to the military along with some more common substances found on the battlefield. GA (soman), GB (sarin), GD (tabun), and VX are chemical nerve agents and HD is the chemical blister agent (mustard). It is well established that these spectral signatures can be exploited to detect and identify chemical agents Hoffland et al., "Spectral Signatures of Chemical Agents and Stimulants", *Optical Engineering* 24(6), pp. 982-984, November/December 1985, incorporated herein by reference.

Figure 3:
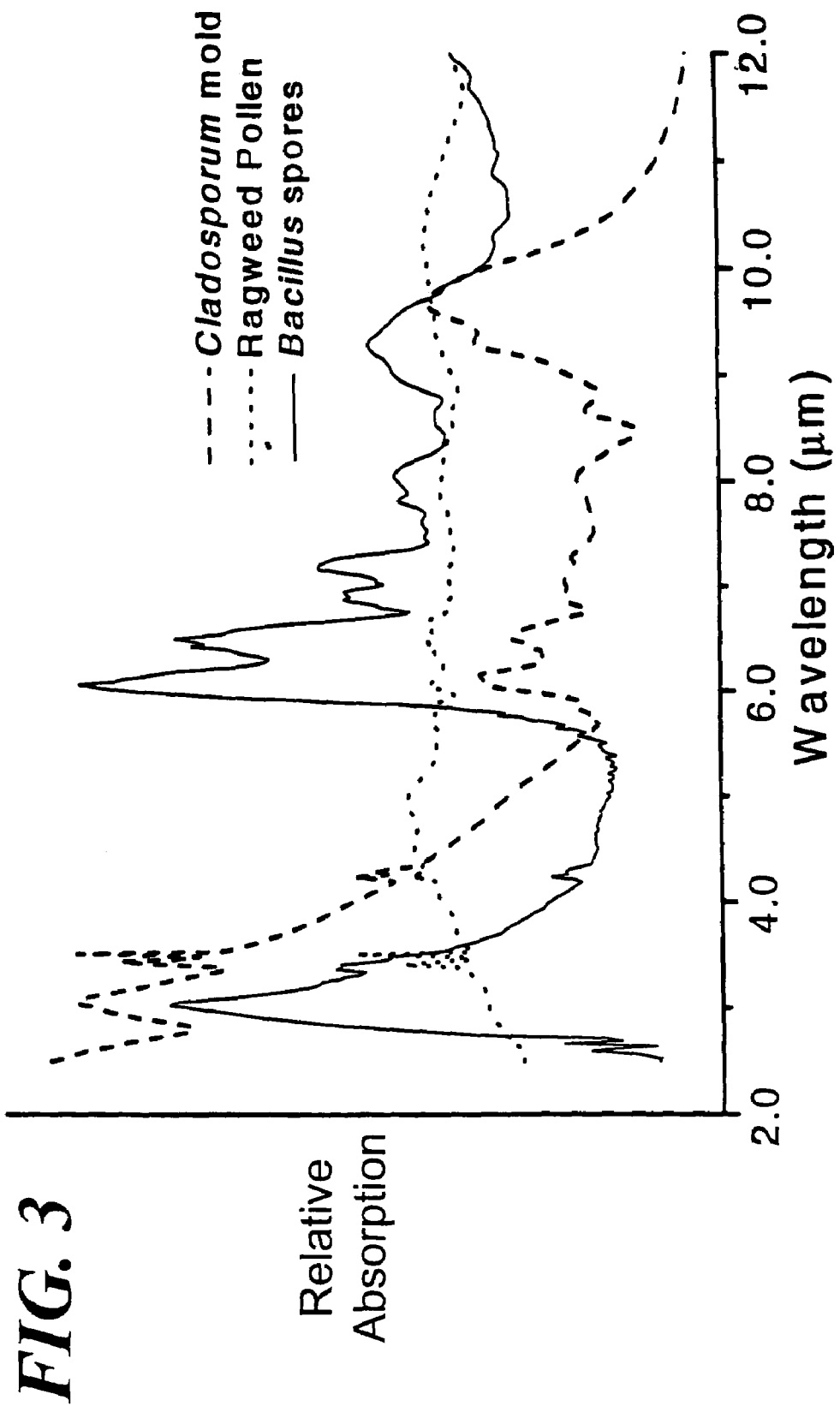
FIG. 3 is a series of infrared spectra of some environmental particulates including pollens, bacteria, and mold particles to demonstrate the capacity of the infrared technique to discriminate among and identify analytes of interest.

FIG. 3 is an infrared spectra of some biological materials found in the atmosphere. There is an extensive body of literature that suggests that the information content in these spectra is adequate to distinguish among different species of bacteria Naumann, "FT-Infrared and FT-Raman Spectroscopy in Biomedical Research", in "*Infrared and Raman Spectroscopy of Biological Materials*", Hans-Ulrich Gremlich and Bing Yan, eds., Marcel-Dekker, Inc., NY 2001.

Modifications and variations of the method and sensor system will be obvious to those skilled in the art from the foregoing detailed description of the invention. It is intended to claim all such changes, modifications, and equivalents as fall within the true spirit and scope of the invention as covered by the appended claims.

What is claimed is:

1. An air sampling sensor system for detection and identification of chemical and biological contaminants, comprising:

(a) substrate feed reel;

(b) a porous adsorptive substrate in the form of a tape;

(c) a substrate uptake reel, said porous adsorptive substrate originating from said feed reel and being advanced from said feed reel to and received by said uptake reel;

(d) a sampling area on a surface of said substrate at an area between said feed reel and said uptake reel;

(e) an air intake for drawing air from the environment containing contaminants through said substrate at said sampling area;

(f) multiple optical or spectrometric interrogation devices for concurrently interrogating said sampling area, wherein said multiple interrogation devices provide independent detection schemes that allow the system to self-confirm identification, and wherein a first interrogation device performs an interrogation along one axis of the substrate and a second interrogation device performs an interrogation along an orthogonal axis to the substrate; and (g) a detector for monitoring the interrogation of said sampling area.

2. The sensor system of claim 1, further comprising:

(a) a focusing optical device for focusing radiation from said interrogation devices on said sampling area; and (b) a focusing optical device for focusing radiation leaving said sampling area onto said detector.

3. The sensor system of claim 1, wherein said air intake is a diaphragm pump.

4. The sensor system of claim 1, further comprising a computer for analyzing the output of said detector.

5. The sensor system of claim 1, wherein said interrogation devices comprise one or more of diffuse reflectance infrared Fourier transform spectroscope, fluorescence spectroscope, ultraviolet/visible spectroscope, near infrared spectroscope, Raman spectroscope, optical dielectric spectroscope, X-ray fluorescence spectroscope, laser-induced breakdown spectroscope.

6. The sensor system of claim 1, wherein said feed reel, said substrate and said uptake reel are in the form of a reel-to-reel cartridge that operates in real time to advance said substrate.

7. The sensor system of claim 1, wherein said substrate is a microporous material that is permeable to air with a surface area to effect accumulation of solid, liquid, aerosol and/or gas phase compounds.

8. The sensor system of claim 1, wherein the substrate is a silver metal membrane filter.

9. The sensor system of claim 1, wherein the substrate is modified to have specific affinity towards the atmospheric constituents of interest.

10. The sensor system of claim 1, further comprising a device for demarcating the surface of said substrate.

11. The sensor system of claim 1, wherein said demarcating device is an optical, mechanical or magnetic demarcating device.

12. The sensor system of claim 1, wherein said detector monitors the accumulation of material on the surface of said substrate.

13. The sensor system of claim 1, wherein said detector triggers an alarm upon detection of programmed contaminants.

14. The sensor system of claim 1, wherein said sampling area is continuously monitored by said interrogation devices and said detector.

15. The sensor system of claim 1, wherein said substrate is advanced from said feed reel to said uptake reel so that a new sampling area is provided.

* * * * *